(12) United States Patent
Birnbaum (10) Patent No.: US 8,142,381 B1
(45) Date of Patent: Mar. 27, 2012

(54) FOOT BRACE DEVICE

(76) Inventor: Bernardo Birnbaum, Miami, FL (US)

( * ) Notice: Subject to any disclaimer, the term of this patent is extended or adjusted under 35 U.S.C. 154(b) by 280 days.

(21) Appl. No.: 12/436,876

(22) Filed: May 7, 2009

(51) Int. Cl.
  *A61F 5/00* (2006.01)
  *A61F 5/37* (2006.01)
  *A43B 13/28* (2006.01)
  *A43B 13/18* (2006.01)

(52) U.S. Cl. ............... 602/23; 602/26; 128/882; 36/27; 36/28

(58) Field of Classification Search ............ 602/23, 602/27, 62–63, 65–66, 5, 16; 36/110, 27, 36/38, 151, 158, 179, 28, 7.8; 128/882; 168/15; 482/79; 53/169, 900; 206/404, 389, 446; 138/128, 156
See application file for complete search history.

(56) References Cited

U.S. PATENT DOCUMENTS

| | | | | |
|---|---|---|---|---|
| 341,327 | A * | 5/1886 | Owen | 166/207 |
| 3,977,094 | A * | 8/1976 | Rivera et al. | 36/7.8 |
| 7,168,186 | B2 * | 1/2007 | Russell | 36/28 |
| 7,303,538 | B2 * | 12/2007 | Grim et al. | 602/23 |
| 7,600,330 | B2 * | 10/2009 | Chen | 36/27 |
| 7,793,431 | B2 * | 9/2010 | Yu | 36/27 |
| 2007/0023955 | A1 * | 2/2007 | Ho | 264/244 |

* cited by examiner

*Primary Examiner* — Patricia Bianco
*Assistant Examiner* — George N Phillips
(74) *Attorney, Agent, or Firm* — Sanchelima & Associates, P.A.

(57) ABSTRACT

A foot brace assembly for immobilizing a user's foot while providing some degree of flexibility through independent shock absorbers that avoid drastic application of loads to the user's foot. A top shoe assembly is coupled through spring members to a bottom shoe assembly that has slightly larger dimensions to receive the top shoe assembly. The underside of the bottom shoe assembly includes rear, middle, and front assemblies that are independent from each other and are compressed depending on the user's gait. The underside of the shoe assembly includes perpendicularly mounted upper tubular members that telescopically receive and guide corresponding lower tubular members that are perpendicularly mounted to the upperside of the sole assembly. The lower tubular members are mounted to depressed walls below the sole assembly's upperside to reduce the effective separation of the shoe and sole assemblies while providing a sufficient guiding distance. Adjustable extension bracing members with corresponding straps are used to secure the foot brace assembly to a user's cast and leg.

8 Claims, 11 Drawing Sheets

Fig 6C

FOOT BRACE DEVICE

BACKGROUND OF THE INVENTION

1. Field of the Invention

The present invention relates to a foot brace device for casts.

2. Description of the Related Art

Several designs for foot brace devices have been designed in the past. None of them, however, includes the ergonometric features disclosed and claimed herein. Conventional foot brace devices are rigid and cause discomfort to the users. The present invention permits a user to wear such a brace that takes into consideration the shifting load points on this device's sole as the user walks.

Additionally, when a cast is placed on a user's foot, the ankle needs to be at a predetermined position. Typically, it is desired to have the foot substantially perpendicular to the axis of the leg. Sometimes, there are some variations in the casting process for a number of reasons. The present invention permits the user to adjust the angular position of the extension bracing members. Otherwise, without this adjustment, a user's tender foot in the cast may not conform to the bottom of the foot brace thus concentrating more weight in one area of the foot than normal. The present invention solves this problem by providing an adjustable feature.

The spring loaded sole assembly provides a soft and relatively delicate landing and exiting load bearing that avoids drastic transmission of a user's weight through the tender areas of the foot being treated. This feature does not exist in foot brace devices known to Applicant.

SUMMARY OF THE INVENTION

It is one of the main objects of the present invention to provide a foot brace device that is ergonometrically compatible with a user not only at rest but also while the user walks.

It is another object of this invention to provide a foot brace device that can be readily mounted and adjusted to a user's foot cast.

It is yet another object of this invention to provide such a device that is inexpensive to manufacture and maintain while retaining its effectiveness.

Further objects of the invention will be brought out in the following part of the specification, wherein detailed description is for the purpose of fully disclosing the invention without placing limitations thereon.

BRIEF DESCRIPTION OF THE DRAWINGS

With the above and other related objects in view, the invention consists in the details of construction and combination of parts as will be more fully understood from the following description, when read in conjunction with the accompanying drawings in which.

DETAILED DESCRIPTION OF THE INVENTION

Figure 1:
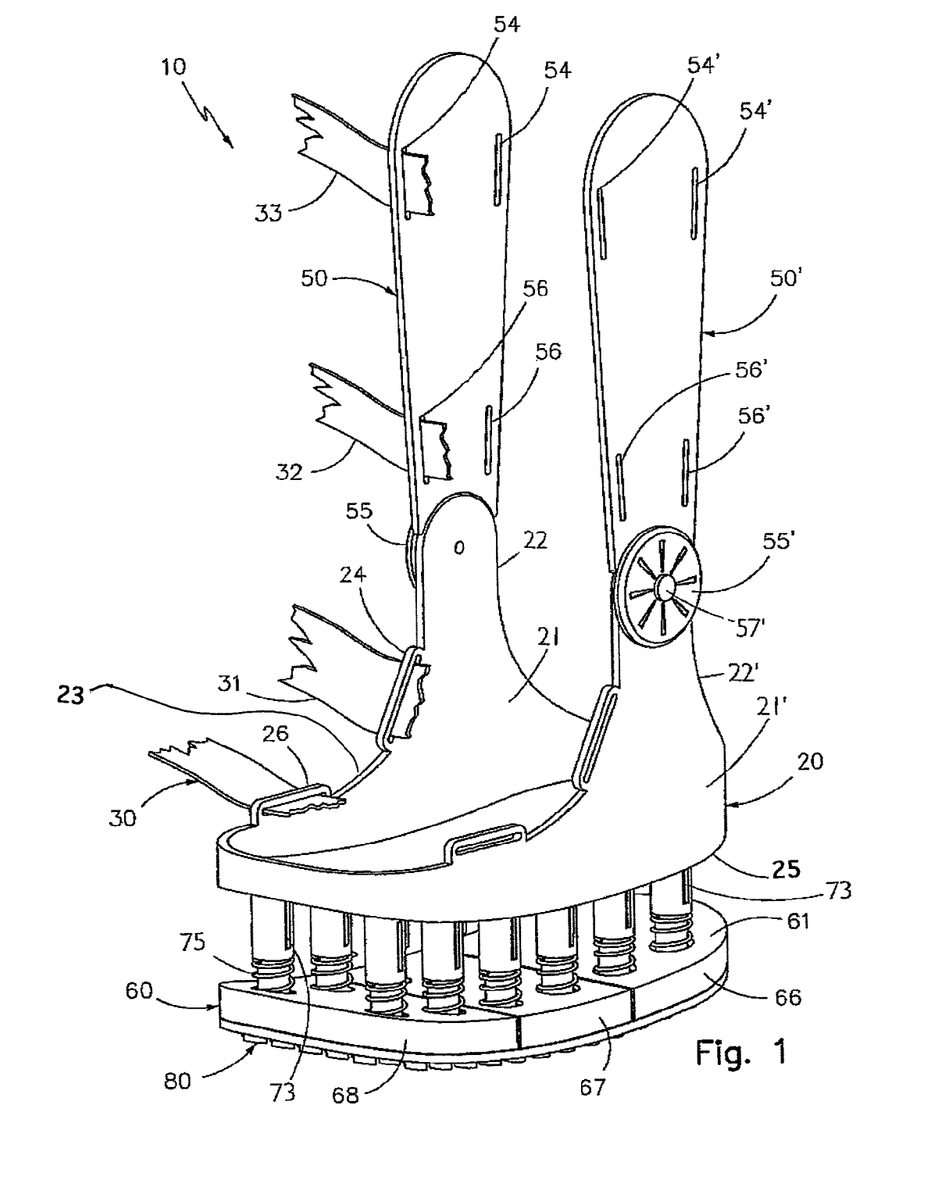
FIG. 1 shows an isometric view of one of the embodiments of the present invention partially showing strap members 30; 31; 32; and 33 used to secure the foot brace to a user's cast. A continuous flexible anti-skid covering 80 is also shown in this embodiment.
Figure 1A:
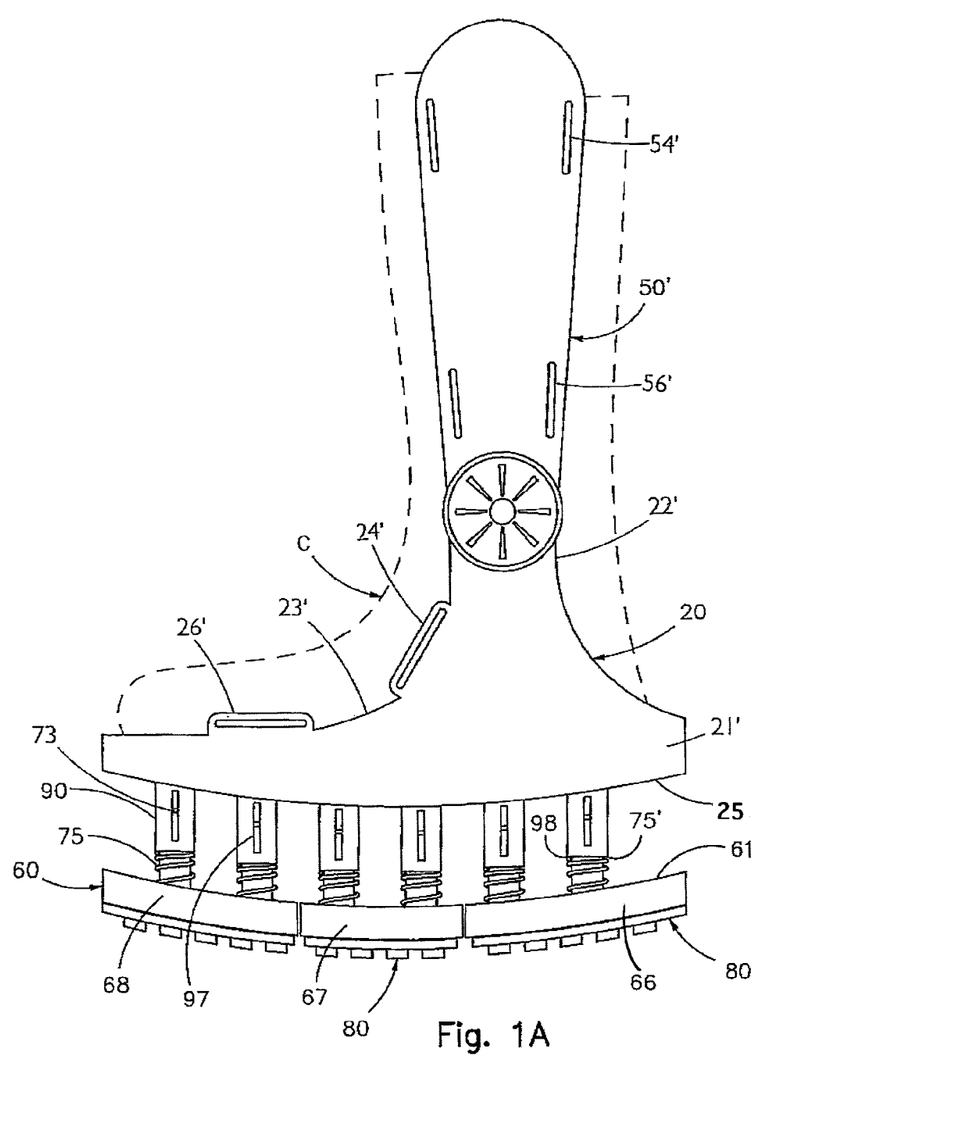
FIG. 1A is an elevational view of a modified embodiment from the one shown in the previous figure wherein anti-skid cover 80 is mounted independently to rear, middle, and front sole members 66; 67; and 68.

Referring now to the drawings, where the present invention is generally referred to with numeral 10, it can be observed that it basically includes top shoe assembly 20, extension bracing members 50, spring biased sole assembly 60, and anti-skid cover 80. In FIG. 1A, the slight curvature of sole assembly 60 is shown in this elevational view resembling the curvature of conventional footwear.

Figure 2:
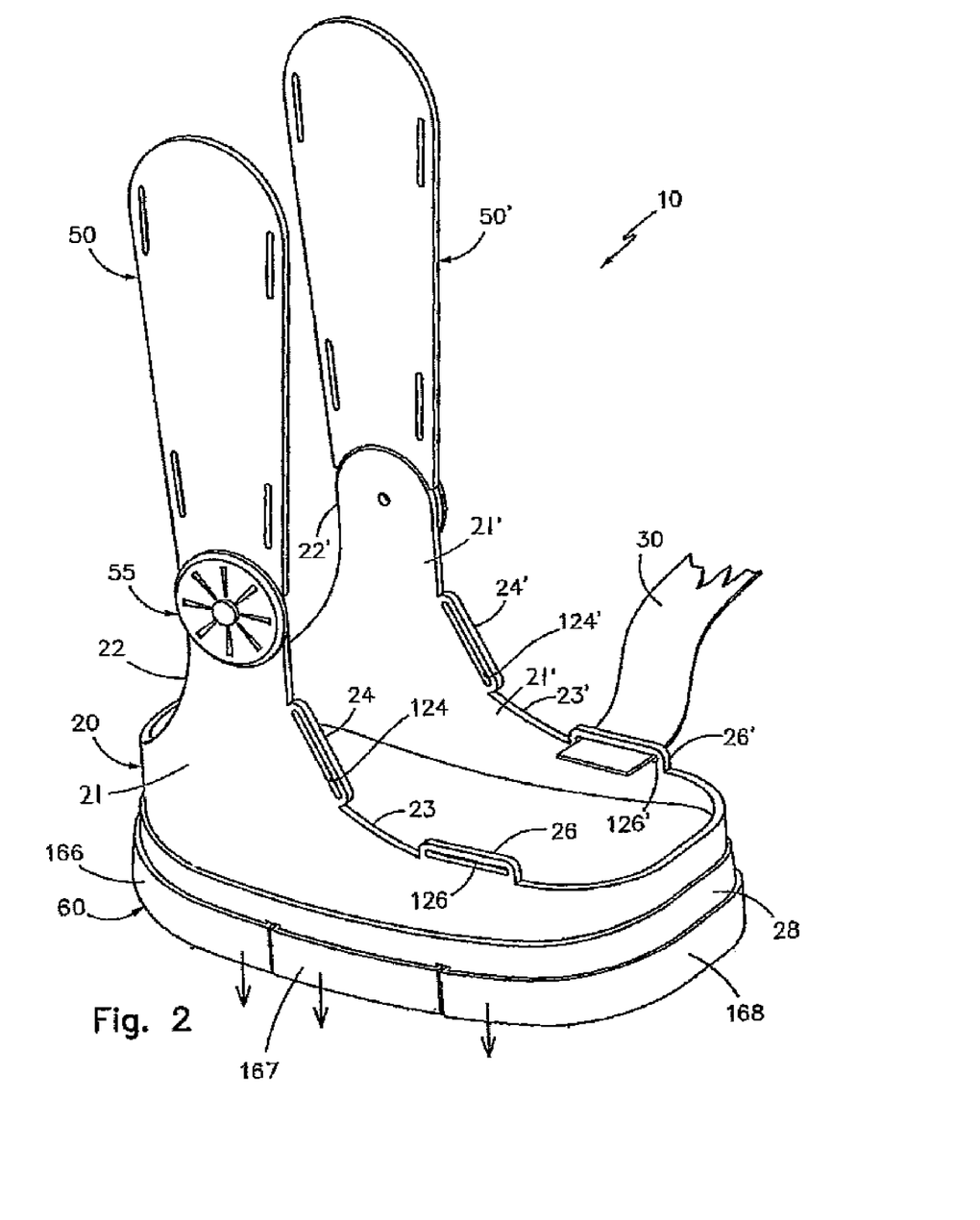
FIG. 2 is an isometric view of the shoe brace shown in the previous figures with slotted peripheral skirt 28 and cooperating peripheral walls 166; 167; and 168 of the rear, middle, and front sole members 66; 67; and 68, respectively, in the compressed position. There is no anti-skid cover in this embodiment.
Figure 2A:
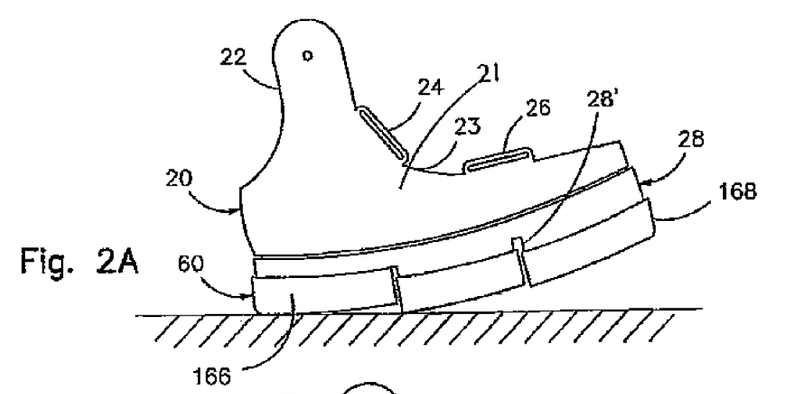
FIG. 2A represents a side elevational view of one of the embodiments of the present invention during heel strike stage of a user's gait.
Figure 2B:
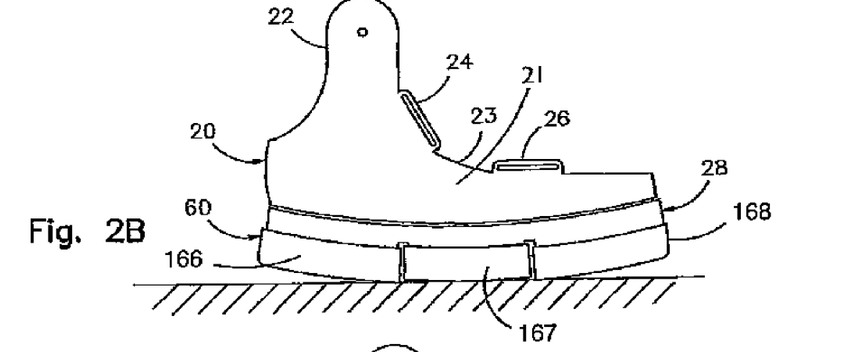
FIG. 2B shows a side elevational view during the mid stance stage.
Figure 2C:
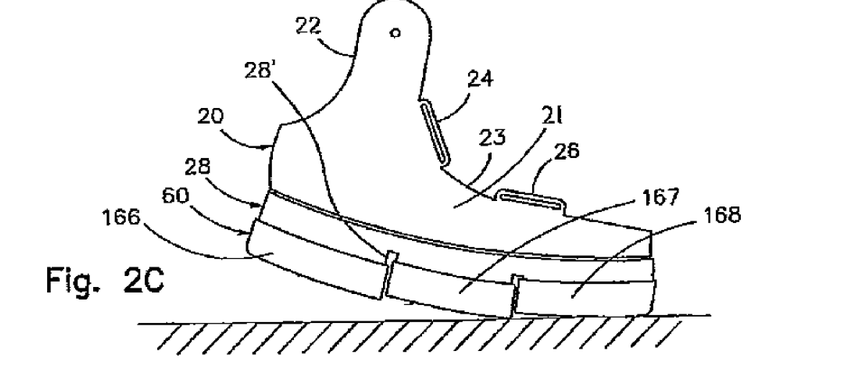
FIG. 2C shows a side elevational view during the heel rise stage of a user's gait.

FIG. 2 shows the foot brace device with the weight force applied in the direction of the arrows with sole assembly 60 brought (compressed) against the bottom surface of shoe assembly 20. In FIGS. 2A; 2B and 2C, the operation of the invention can be appreciated as the figures represent the approach, complete support, and exit of the user's load through foot brace device 10. The rear, middle, and front sole members 66; 67; and 68 act as shock absorbers to sequentially and gradually transmit the user's weight avoiding drastic forces.

Figure 3:
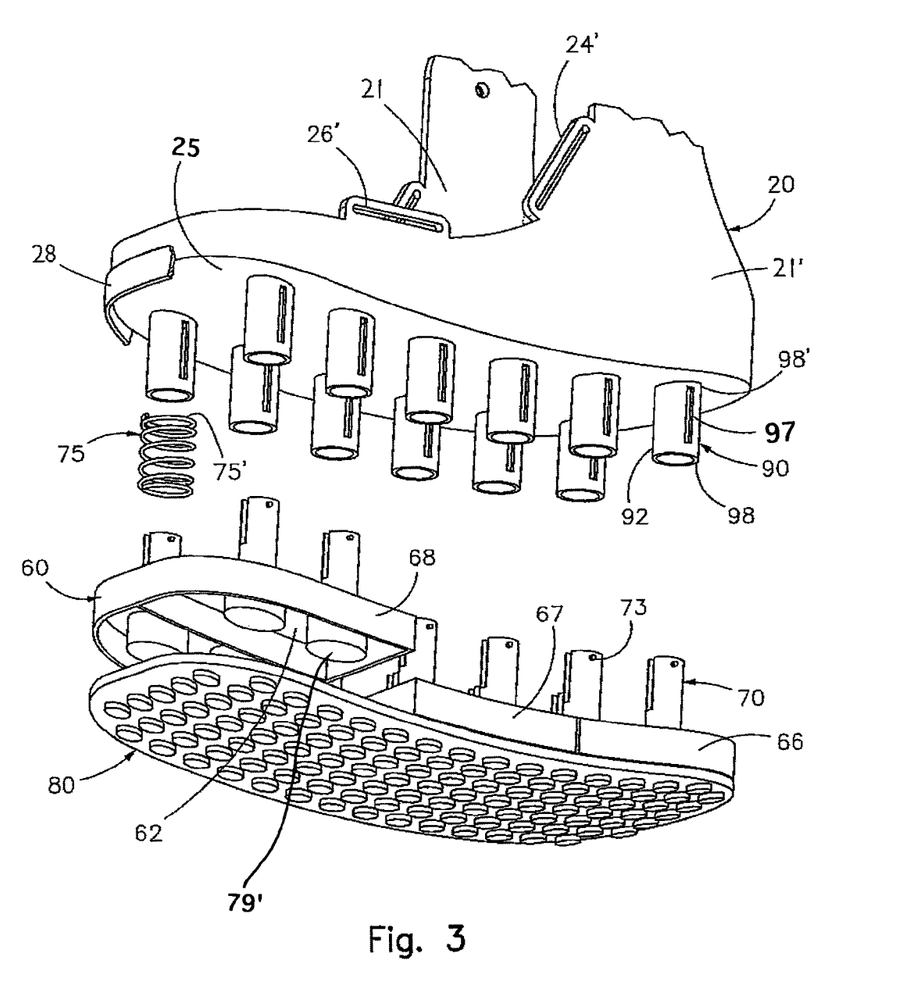
FIG. 3 is an exploded partial isometric view of top shoe assembly 20 and spring biased sole assembly 60 with a partial representation of skirt 28.

Top shoe assembly 20 is made of a substantially rigid material to provide support for the foot and ankle cast C and includes ear members 22 and 22', loop members 24; 24'; 26; and 26', and peripheral skirt 28, as best seen in FIG. 2. As shown in FIG. 3, skirt 28 is peripherally mounted to lateral portions 21 and 21'. Ear members 22 and 22' extend vertically from the upper edges 23; 23' of lateral portions 21; 21' of top shoe assembly 20. Loop members 24; 24'; 26; and 26' have respective through openings 124; 124'; 126; and 126' that receive strap members 30 and 31, or equivalent means, to secure top shoe assembly 20 to a user's cast C, as seen in FIGS. 1 and 1A. Skirt 28 extends vertically downwardly from the bottom of shoe assembly 20 and has cooperative dimensions to fit within rear, middle, and front peripheral walls 166; 167; and 168. Peripheral walls 166; 167; and 168 are mounted to the outside surfaces of rear, middle, and front members 66; 67; and 68, respectively. Skirt 28 and peripheral walls 166; 167; and 168 cooperate to hide the internal components (lower and upper tubular guides 70 and 90, etc.) and also prevent extraneous matter from coming in contact with these moving parts.

Figure 5:
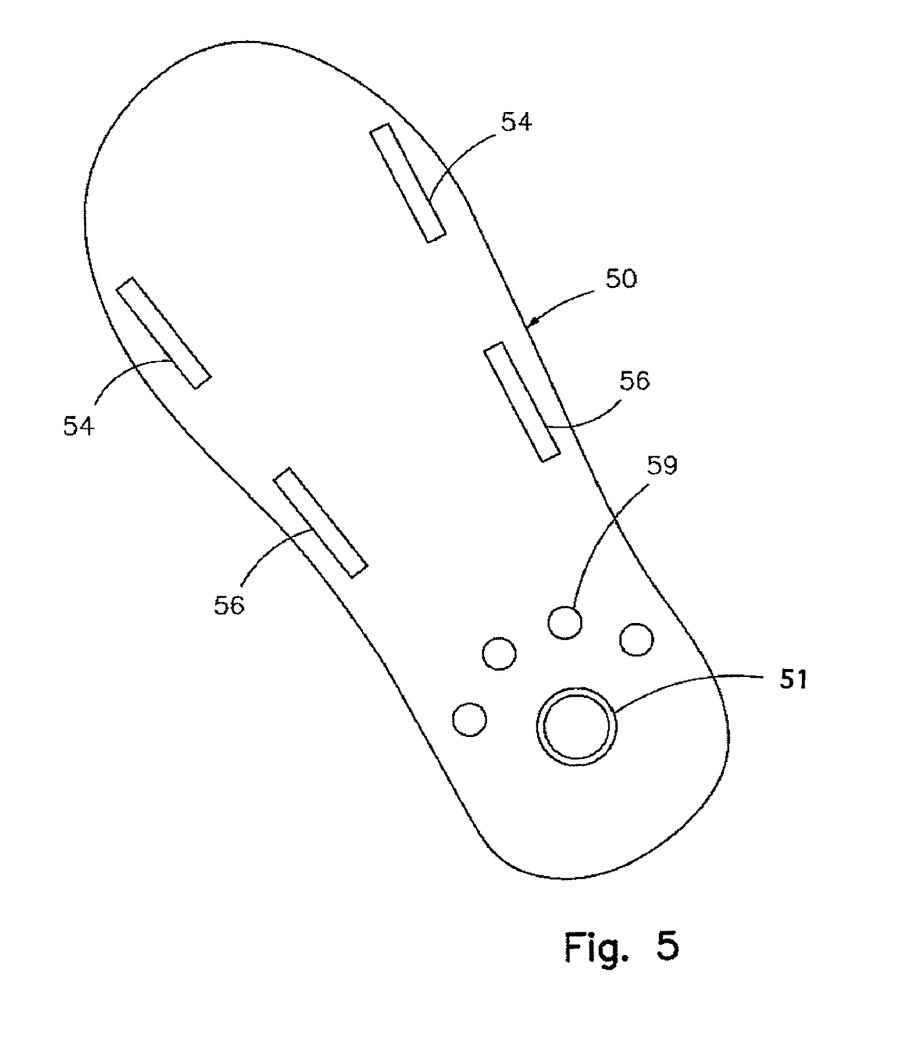
FIG. 5 is an elevational view of one of the adjustable extension bracing members used in the embodiments of the present invention shown in the previous figures.
Figures 5A, 5B:
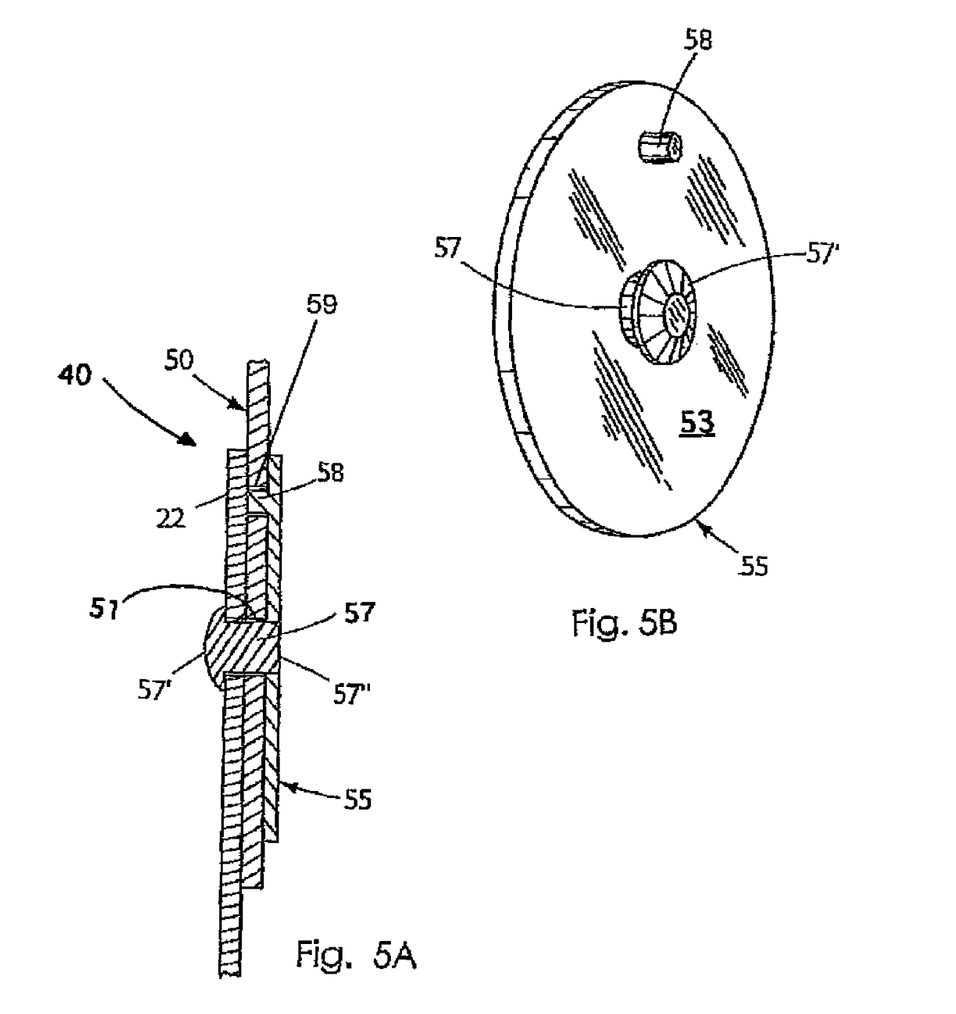
FIG. 5A is a partial cross-sectional elevation of the adjustment mechanism used in one of the embodiments.
FIG. 5B shows an isometric view of the locking wheel used in the embodiment for the adjustment mechanism shown in the previous figure.

Extension bracing members 50 and 50' are pivotally mounted to the upper ends of ear members 22 and 22', respectively, to move within their own planes. Members 50 and 50' adjust to a comfortable angle of a user's cast C with adjustment mechanism 40. Members 50 and 50' include through slots 54; 54'; 56; and 56' to receive strap members 32 and 33 therethrough, as best seen in FIG. 1. Adjustment mechanism 40 can be implemented in several ways. One of these embodiments for mechanism 40 includes through opening 51, as shown in FIG. 5, which receives headed shaft 57 of locking wheel 55 (and 55'), as shown in FIGS. 1 through 2 and 5B. Shaft 57 includes head 57'. End 57" of shaft 57, when the latter is installed, remains flush with internal surface 53 of wheel 55, as best seen in FIG. 5A. End 57" can be glued to wheel 55, or shaft 57 can also be integral to wheel 55 if head 57' is deformable. Wheel 55 includes locking pin 58 that engages through one of the through holes 59 in extension bracing member 50.

Figure 6:
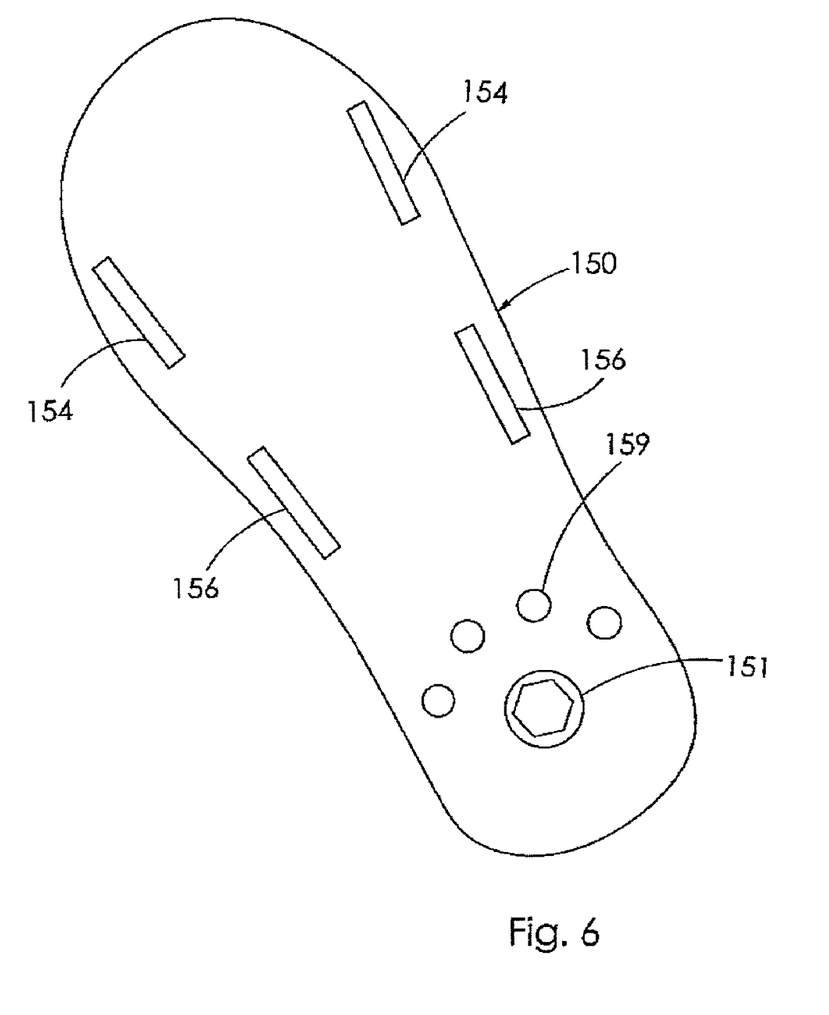
FIG. 6 is a side elevational view of another extension bracing member.
Figure 6A:
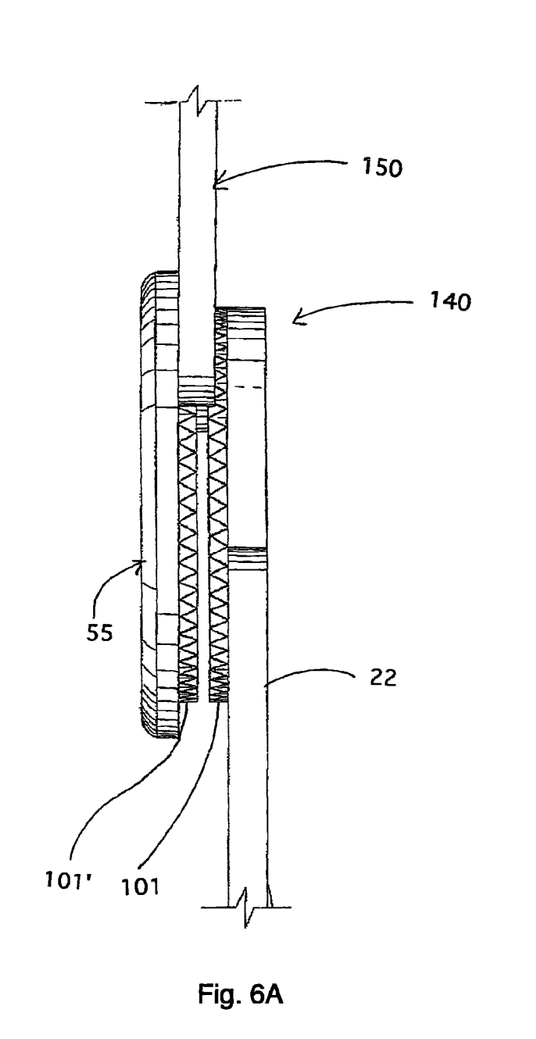
FIG. 6A is a partial elevational view of another embodiment for an adjustment mechanism with the teeth disengaged.
Figure 6B:
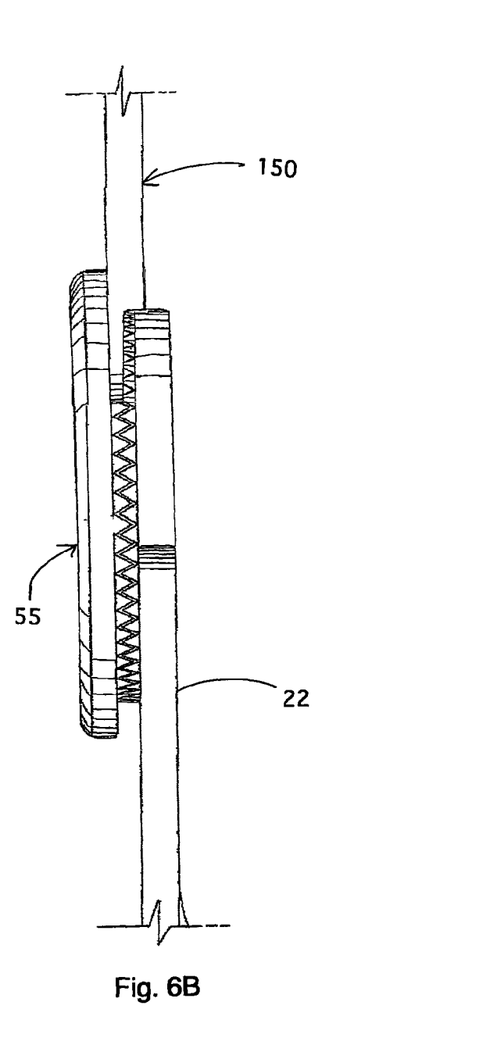
FIG. 6B is similar to the previous figure except that the teeth are engaged.
Figure 6C:
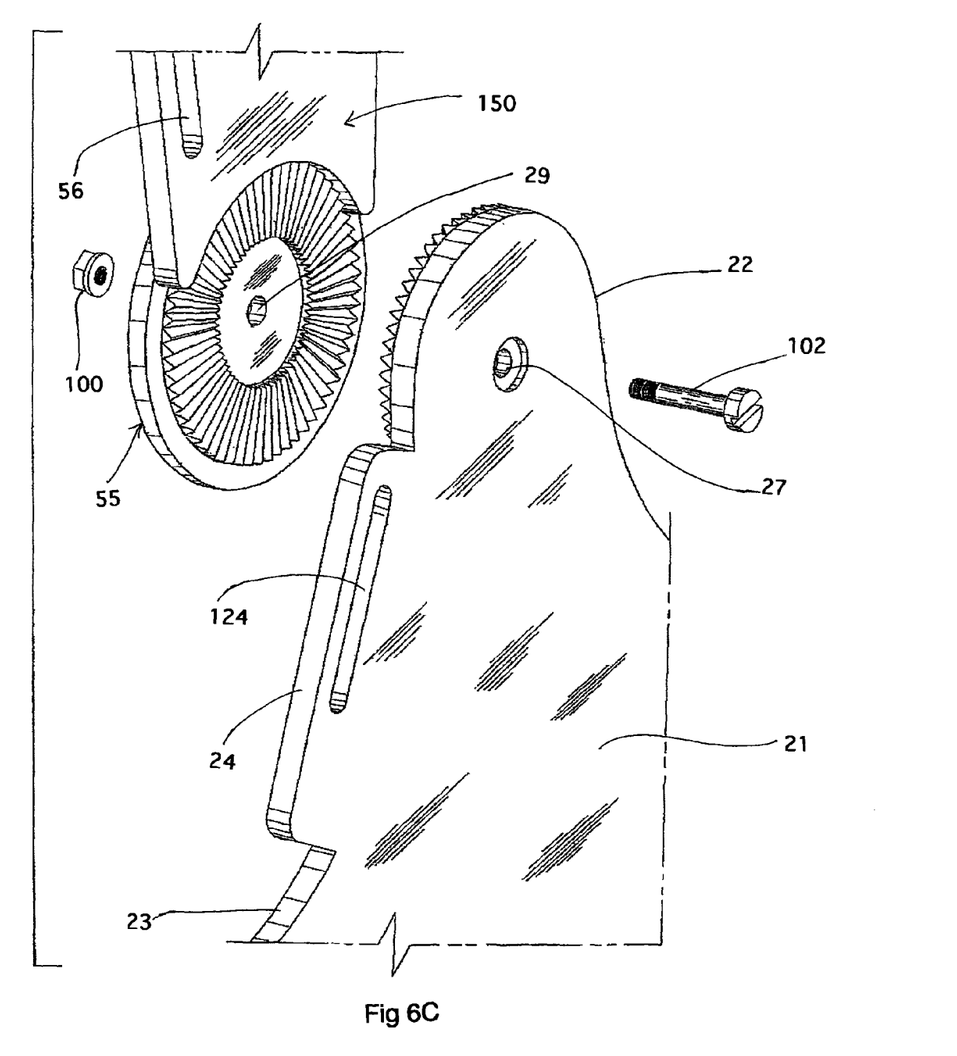
FIG. 6C is a partial isometric exploded view of the embodiment shown in the previous two figures.

Another embodiment for an adjustment mechanism is referred to with numeral 140 in FIGS. 6A; 6B; and 6C. Extension 150, as shown in FIG. 6, is used with opening 151 that has a hexagonal shape to receive nut 100 therethrough. Cooperating bolt 102 is inserted through holes 27 and 29 in FIG. 6C to be received by nut 100 and cause teeth 101 and 101' to come towards each other. A user can then adjust the angle of extension of 150 with respect to ear 22. Slots 154 and 156 function like slots 54 and 56 in FIG. 5. Through holes 159 functions like through holes 59 in the embodiment shown in FIG. 5.

Figure 4:
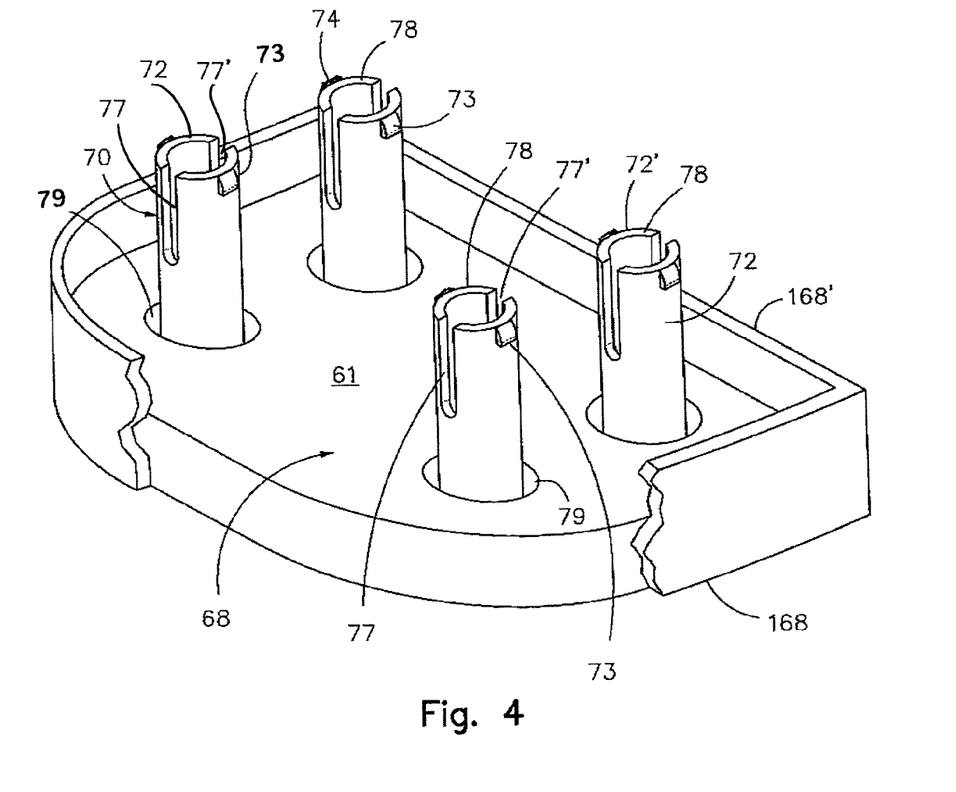
FIG. 4 is a partial isometric view of the front sole member 68 shown in the previous figures with partially broken front peripheral wall 168.

Spring biased sole assembly 60 has a predominantly rectangular shape overstating a user's footprint, as best seen in FIG. 2. Assembly 60, in one of the embodiments, includes three sole members, namely, rear, middle, and front sole members 66; 67; and 68 with corresponding peripheral walls 166; 167; and 168, respectively. These peripheral walls have cooperative dimensions to receive peripheral skirt 28 within their periphery. Cut outs or channels 28' are cooperatively positioned to permit the transversal portions of walls 166; 167; and 168 to travel therethrough, as best seen in FIGS. 2A; 2B; and 2C. Cutouts 28' also act as a guide to keep walls 166; 167; and 168 traveling along a vertical path. One of these transversal portions is represented in FIG. 4 and referenced with numeral 168'.

Assembly 60 has an upperside 61 and an underside 62, as shown in FIGS. 1 and 3, respectively. Lower tubular members 70 are perpendicularly mounted to upperside 61. As best seen in FIG. 4, lower tubular members 70 have a preferably cylindrical shape, in this embodiment, and each includes longitudinal slots 77 and 77', opposite to each other, defining bifurcated walls 72 and 72'. Guiding protrusion 73 resembles an arrowhead with a slanted surface. Slots 77 and 77' extend from the distal end 78 of lower tubular members 70 towards the other end a predetermined distance. Slots 77 and 77' permit the inward and resilient deflection of distal portions of walls 72 and 72' of members 70. The other end of lower tubular members 70 is centrally mounted inside cooperating recessed cavity 79. Cavity 79 has a diameter that is sufficiently larger than the diameter of lower tubular member 70 to also coaxially receive helical spring 75 therein. Spring 75 is wound around member 70 with one end resting against the bottom 79' of recessed cavity 79. The other end 75' of spring 75 coacts against end surface 98 of member 90, as shown in FIG. 1A.

Upper tubular assemblies 90 include tubular guide members 92 with ends 98 and 98', as seen in FIG. 3. Assemblies 90 are perpendicularly and rigidly mounted to underside 25 of shoe assembly 20. In the embodiment shown in FIG. 3, slots 97 extend centrally along tubular guide members 92 and end at a predetermined distance from end 98, as seen in FIG. 1A. Slots 97 have cooperative dimensions to receive guiding protrusions 73 and 74 that are cammingly deflected when members 70 are inserted inside assemblies 90.

Anti-skid cover 80 is optionally mounted to the underside of assembly 60. Cover 80 is flexible enough to permit the transmission of the weight of a user to rear, middle, and front sole members 66; 67; and 68. Cover 80 can be implemented as a continuous sheet, as shown in FIG. 1, or limited to members 66; 67; and 68, as shown in FIG. 1A.

The foregoing description conveys the best understanding of the objectives and advantages of the present invention. Different embodiments may be made of the inventive concept of this invention. It is to be understood that all matter disclosed herein is to be interpreted merely as illustrative, and not in a limiting sense.

What is claimed is:

1. A foot brace device, comprising:
   A) a shoe assembly having a bottom wall with a first underside, a first upperside and a peripherally extending wall perpendicular to said bottom wall adapted to receive therein a user's foot cast, said shoe assembly having a front end and a rear end with two opposite ear portions extending from said peripherally extending wall away from said bottom wall, said ear portions being adjacent to said rear end;
   B) a sole assembly having substantially the same projected dimensions as said shoe assembly and further including a second upperside and a second underside, spring biased means for mounting said sole assembly to said first underside, said sole assembly having moving independent rear, middle, and front portions that are brought against said first underside when a user applies his or her weight during his or her entry gait, bearing weight and exit gait, proportionally to the weight applied thereby sequentially and gradually absorbing the application of said user's weight load;
   C) two opposite parallel and spaced apart extension flat bracing members, each defining a plane and each pivotally and adjustably mounted to each of said ear portions to move over said respective planes a predetermined angular range adapted to the characteristics of said foot cast; and
   D) strap means for securing said shoe assembly and extension bracing members to a user's foot cast and leg, and said spring biased means includes a plurality of upper tubular guide members perpendicularly and rigidly mounted to said first underside and each of said upper tubular guide members including a distal end surface and a centrally disposed slot starting at a predetermined distance from said end surface, and said spring biased means further including a corresponding plurality of lower tubular members perpendicularly and rigidly mounted to said second upperside and being receivable within said upper tubular guide members and each of said lower tubular members including a resilient guiding protrusion mounted exteriorly on said lower tubular members for cooperative cammingly insertion within said upper tubular guide members and for subsequent lodging said protrusion within said slots to correspondingly limit the telescopic travel of said upper tubular guide members and lower tubular members within a predetermined distance, wherein said spring biased means includes a corresponding plurality of spring members having first and second ends with a helical shape that receive therein said lower tubular members and said first end coacting with said second upperside and said second end coacting with said distal end surface to urge said sole assembly to separate from said shoe assembly.

2. The device set forth in claim 1 wherein said lower tubular members are bifurcated defining two opposite walls disposed at a parallel and spaced apart relationship with respect to each other to permit a slight resilient inwardly deflection of said walls thereby facilitating the cammingly insertion of said protrusions within said upper tubular guide members.

3. The device set forth in claim 2 wherein said rear, middle and front portions of said sole assembly are independent from each other and each of said portions has at least one of said lower tubular members.

4. The device set forth in claim 3 further including:
E) flexible means for covering each of said rear, middle, and front portions.

5. The device set forth in claim 4 wherein said lower tubular members are centrally mounted within a recessed cavity on said second upperside.

6. The device set forth in claim 5 wherein said spring biased means includes a corresponding plurality of spring members having first and second ends with a helical shape that receive therein said lower tubular members and said first end coacting with said second upperside and said distal end surface to urge said sole assembly to separate from said shoe assembly.

7. The device set forth in claim 6 further including:
F) flexible means for uninterruptedly covering said rear, middle, and front portions.

8. The device set forth in claim 7 further including a skirt mounted exteriorly and peripherally to said shoe assembly and said sole assembly further including cooperating rear, middle, and front peripheral walls exteriorly mounted to said rear, middle, and front portions, respectively, so that said skirt is receivable within said rear, middle, and front peripheral walls.

\* \* \* \* \*